United States Patent [19]

Nakazora et al.

[11] Patent Number: 5,233,098
[45] Date of Patent: Aug. 3, 1993

[54] METHOD FOR REMOVING AND RECOVERING FLUORINATED ALCOHOL FROM WASTE GAS

[75] Inventors: Toru Nakazora; Toshihiro Nakamichi; Tuneyoshi Hisayuki; Katumi Takesita, all of Ube; Yutaka Katsuhara, Kawagoe, all of Japan

[73] Assignee: Central Glass Company, Limited, Yamaguchi, Japan

[21] Appl. No.: 898,360

[22] Filed: Jun. 12, 1992

Related U.S. Application Data

[63] Continuation of Ser. No. 704,955, May 23, 1991, abandoned.

[30] Foreign Application Priority Data

May 30, 1990 [JP] Japan .................................. 2-140901
Jun. 20, 1990 [JP] Japan .................................. 2-161552

[51] Int. Cl.$^5$ ............................................. C07C 31/34
[52] U.S. Cl. .................................... 568/842; 568/921; 568/923; 55/220; 55/244
[58] Field of Search ...................... 568/842, 921, 923; 55/220, 244

[56] References Cited

U.S. PATENT DOCUMENTS 3,151,171 9/1964 Day ..................................... 568/842
3,317,616 5/1967 Weinmayr ........................... 568/842

FOREIGN PATENT DOCUMENTS 50-28387 9/1975 Japan .
1-245838A 10/1989 Japan .

OTHER PUBLICATIONS

*Websters II New Riverside University Dictionary*, Houghton Mifflin Company, Boston, 1984, p. 92.
*Hackhs Chemical Dictionary*, Mc Graw Hill, New York, 1969, p. 26.

Primary Examiner—Marianne M. Cintins
Assistant Examiner—Rebecca Cook
Attorney, Agent, or Firm—Keck, Mahin & Cate

[57] ABSTRACT

A method for removing a perfluoroalkyl alcohol from a waste gas and recovering the perfluoroalkyl alcohol comprising the steps of bringing the waste gas into contact with an aqueous alkaline solution thereby to absorb the perfluoroalkyl alcohol into said solution and consequently obtain an aqueous alkaline solution containing an alkoxide of the perfluoroalkyl alcohol. Adding an acid to the aqueous alkaline solution containing the alkoxide of the perfluoroalkyl alcohol until the alkaline solution turns into an acidic solution with a pH value smaller than 5, thereby to turn said alkoxide into said perfluoroalkyl alcohol and subjecting the acidic solution to distillation to recover the perfluoroalkyl alcohol.

16 Claims, No Drawings

METHOD FOR REMOVING AND RECOVERING FLUORINATED ALCOHOL FROM WASTE GAS

This application is a continuation of application Ser. No. 07/704,955, filed May 23, 1991 now abandoned.

BACKGROUND OF THE INVENTION

This invention relates to a method for removing fluorinated alcohols such as fluoroalkyl alcohols used as industrial solvents from waste gases and, according to the need, recovering the fluorinated alcohols after separating from the waste gases.

Fluoroalkyl alcohols serve as good solvents for various polymers including so-called engineering plastics such as polyamides, polyesters and polyacetals. Recently a fluoroalkyl alcohol is often used as an industrial solvent in the process of coating a polymer on, for example, metal or ceramic substrates as the solvent for the polymer. After the application of the polymer solution to the substrates the solvent is dissipated by drying with a large volume of air. Since fluoroalkyl alcohols are harmful substances having a peculiar odor, it is desirable to remove the fluoroalkyl alcohol from the waste gas of the coating and drying operations before discharging the waste gas into the atmosphere. However, the concentration of the fluoroalkyl alcohol in the waste gas is usually very low, e.g. of the order of $10^3$ ppm, and it is difficult to clean the waste gas so as to render the gas odorless by a conventional treatment for removing or recovering organic solvents.

There is no established method for efficiently separating fluorinated alcohols from waste gases. For the treatment of waste gases containing more popular organic solvents, there are several kinds of methods such as adsorption by activated carbon, condensation by cooling, absorption in liquids and combustion. However, for the treatment of gases containing fluoroalkyl alcohols these methods have some disadvantages, respectively. In the case of adsorption by activated carbon it is necessary to alternate adsorption and desorption at short intervals because of relatively small adsorption capacity of the adsorbent. Besides, there is the need of using a large quantity of steam for the desorption, so that if the adsorbed organic solvent is soluble in water the solvent is recovered in the form of a very dilute aqueous solution. In the case of condensation by cooling, it is necessary to greatly lower the gas temperature when the concentration of a fluoroalkyl alcohol in the gas is very low, and this is unfavorable for the saving of energy. In the case of combustion there is the problem of corrosion of the furnace by the action of hydrogen fluoride formed by the combustion of fluoroalkyl alcohols.

As to absorption of organic halogen compounds into liquids, there are proposals of using a selected organic solvent as the absorbent, such as JP 50-28387 and JP 1-245838. However, these methods generally involve a problem that vapor of the organic solvent used as the absorbent is liable to intrude into the waste gas under treatment. As another problem, in the case of physical absorption of a fluoroalkyl alcohol with water or an organic solvent the absorption soon reaches saturation because only a very small amount of the fluoroalkyl alcohol can be absorbed, so that the fluoroalkyl alcohol is liable to be liberated into the atmosphere.

Fluorinated alcohols are expensive materials. In the industrial practice of the separation of a fluorinated alcohol from a waste gas it is desirable that the separated alcohol can easily be recovered for reusing it.

SUMMARY OF THE INVENTION

It is an object of the present invention to provide a method for easily and efficiently removing fluorinated alcohols, and particularly fluoroalkyl alcohols, from waste gases.

It is another object of the invention to provide a method for easily and efficiently removing a fluorinated alcohol, particularly a fluoroalkyl alcohol, from a waste gas and easily recovering the alcohol separated from the waste gas at good yield and high purity.

We have discovered that when a waste gas containing a fluorinated alcohol is brought into contact with an aqueous basic solution, the fluorinated alcohol is easily absorbed into the aqueous solution to form an alkoxide which is odorless and exhibits high solubility in water.

The present invention is very suitable for application to waste gases containing a fluoroalkyl alcohol represented by the general formula (1) or the general formula (2):

$$RfCH_2OH \qquad (1)$$

where Rf represents a perfluoroalkyl group having 1 to 10 carbon atoms, $$RfRf'CHOH \qquad (2)$$

where each of Rf and Rf' represents a perfluoroalkyl group having 1 to 10 carbon atoms.

From an industrial point of view, trifluoroethanol $CF_3CH_2OH$, pentafluoropropanol $CF_3CF_2CH_2OH$ and hexafluoroisopropanol $(CF_3)_2CHOH$ are representatives of fluoroalkyl alcohols of the general formulas (1) and (2), and any of these alcohols can efficiently be separated from waste gases by the method according to the invention. In particular hexafluoroisopropanol is an excellent solvent for many kinds of industrially useful polymers.

A preferred example of the aforementioned aqueous basic solution is a solution of sodium or potassium hydroxide.

The present invention utilizes a chemical reaction between the fluorinated alcohol in the waste gas and the aqueous basic solution. By the reaction the alcohol turns into a fluorine-containing alkoxide which is odorless, and this alkoxide is so high in solubility in water that the waste gas cleaning operation can stably be performed without suffering from precipitation of the reaction product. Although the fluorinated alcohol is a good solvent for various polymers, the alkoxide formed in the aqueous solution does not dissolve polymers useful as plastic materials. Therefore, the material of the absorption apparatus can be selected from not only metals, but also relatively inexpensive plastics.

The present invention includes recovering the fluorinated alcohol from the aqueous solution used for removing the alcohol from a waste gas, by treating the aqueous basic solution with an acid such that the solution turns into an acidic aqueous solution and then subjecting the acidified solution to distillation. A suitable acid for use is an inexpensive inorganic acid such as sulfuric acid or hydrochloric acid.

The fluoroalkyl alcohols mentioned hereinbefore have boiling points lower than the boiling point of water, and none of them form azeotropes with water.

Therefore, it is possible to recover any of these fluoroalkyl alcohols at high purity and good yield by carrying out precision distillation of the afore-mentioned acidic aqueous solution in an ordinary manner to distil out the alcohol from the top of the distillation tower.

DESCRIPTION OF THE PREFERRED EMBODIMENTS

An aqueous solution used in this invention is an aqueous solution of hydroxide or carbonate of an alkali metal or an alkaline earth metal or an aqueous solution of ammonia. In industrial practice it is suitable to use either sodium hydroxide or potassium hydroxide in view of inexpensiveness.

The concentration of the aqueous basic solution is not strictly limited and may range from 1 to 60 wt %. A preferred range of the concentration is from 5 to 30 wt %. When a sodium hydroxide solution of a relatively high concentration is used, there is the possibility of precipitation of sodium hydrogen carbonate resulting from absorption of carbon dioxide contained in air, but this raises little problem because sodium hydrogen carbonate is decomposed by the absorbed fluorinated alcohol to result in liberation and dissipation of carbon dioxide gas and vanishment of the precipitate.

The contact of a waste gas containing a fluorinated alcohol with the aqueous basic solution can be made at an arbitrary temperature, and it suffices to perform the operation at room temperature. The manner of the contact is not limited. In most cases it is suitable to use a washing tower packed with an inactive material for dispersing fluids, such as Raschig rings, so as to realize efficient contact between the waste gas flowing upward and the aqueous basic solution flowing downward. It is possible to reduce the concentration of the fluorinated alcohol in the treated waste gas to 100 ppm or below by a single-stage absorption operation, and it is optional to accomplish further removal of the fluorinated alcohol by a two-stage or further multi-stage absorption operation.

The absorption method according to the invention is illustrated by the following nonlimitative examples.

EXAMPLE 1

This example relates to the removal of hexafluoroisopropanol (HFIP) from a waste gas by using a single-stage washing apparatus.

A glass cylinder having an inner diameter of 45 mm was used as the body of a packed tower, and polyethylene Raschig rings 6 mm in outer diameter and 6 mm in length were packed in the glass cylinder such that the height of the packing section became 300 mm. A gas fed pipe was to the packed tower at an inlet in a bottom section in order to pass a waste gas through the packed section toward an outlet in a top section. An basic solution tank was positioned at the level of the bottom of the packed tower, and the tower was provided with a circulating pump and piping in order to flow the basic solution from the top section of the tower through the packed section and then into the tank. That is, in the packed tower the waste gas flowing upward comes into efficient contact with the basic solution flowing downward.

As a simulated waste gas, air containing a predetermined amount of HFIP was passed through the packed tower at a flow rate of 2 m$^3$/hr, and simultaneously 1 liter of 10 wt % aqueous solution of NaOH was circulated through the packed tower at a flow rate of 30 l/hr.

When the concentration of HFIP in the simulated waste gas at the inlet to the packed tower was 1000 ppm the concentration of HFIP in the washed gas at the outlet in the top section of the tower became 10 ppm. When the initial concentration of HFIP was increased to 2000 ppm, the concentration of HFIP in the washed gas at the outlet became 30 ppm. When the initial concentration of HFIP was further increased to 5000 ppm the concentration of HFIP at the outlet became 35 ppm.

The test using air containing 2000 ppm of HFIP was continued for a long time under the same operation condition. In the washed gas at the outlet of the packed tower the concentration of HFIP remained at about 30 ppm, but after the lapse of about 20 hr the sodium hydroxide solution (1 liter) almost lost the ability to absorb HFIP.

EXAMPLE 2

Using the same apparatus as in Example 1, air containing 2000 ppm of HFIP was washed with 20 wt % aqueous solution of KOH under the same operation conditions as in Example 1. In the washed gas at the outlet of the packed tower the concentration of HFIP became lower than 30 ppm.

COMPARATIVE EXAMPLE

The washing operation of Example 2 was modified by using water in place of the NaOH solution. In this case the concentration of HFIP in the gas at the outlet of the tower was 2000 ppm, meaning little removal of HFIP from the gas introduced into the packed tower.

EXAMPLE 3

The packed tower described used in Example 1 was combined with another packed tower of the same design in a series arrangement so as to construct a two-stage washing apparatus. One liter of 10 wt % aqueous solution of NaOH was prepared for each of the two packed towers, and the solution was circulated through each tower at a rate of 30 l/hr, while air containing 2000 ppm of HFIP was passed through the two packed towers in turn. At the outlet of the second-stage packed tower the concentration of HFIP in the washed gas was below 10 ppm.

EXAMPLE 4

Using the same apparatus as in Example 1, air containing 2000 ppm of trifluoroethanol was passed through the packed tower at a flow rate of 2 m$^3$/hr, while 1 liter of 10 wt % aqueous solution of NaOH was circulated at a flow rate of 30 l/hr. In the washed gas at the outlet of the tower the concentration of trifluoroethanol became 80 ppm.

The above described absorption operation gives an aqueous basic solution in which a fluorinated alcohol is present in the form of alkoxide. To recover the alcohol from this solution, the first step is turning the alkoxide into the original alcohol by adding an acid to the solution. The acid can be selected from inorganic acids such as hydrochloric acid, sulfuric acid, nitric acid, etc., and usually it is favorable to use relatively inexpensive hydrochloric acid or sulfuric acid.

As an acid is added to the basic solution first there occurs neutralization of excess base at pH of 11 to 10, and as the acid is further added until pH of the solution reaches 6 to 5 the alkoxide reverts to the original alcohol. Therefore, it is possible to obtain an aqueous solution containing the fluorinated alcohol in a free state by adjusting pH of the aqueous basic solution used in the absorption operation. For example, in the case of neutralizing 1 liter of an aqueous solution containing 2.0 mol of sodium hydroxide and 1.0 mol of HFIP with 20% hydrochloric acid there are two equivalent points, one at pH of 10.7 and another at pH of 5.5. That is, excess sodium hydroxide is neutralized at pH of 10.7, and the alkoxide of HFIP reverts to free HFIP at pH of 5.5. Therefore, an aqueous solution containing free HFIP is obtained by adding an acid to the aqueous basic solution until pH of the solution becomes below 5.5.

The next step is distilling the acidic solution containing the freed alcohol. There is no particular restriction on the apparatus for distillation. It suffices to use a conventional precision distillation apparatus. If the concentration of the fluorinated alcohol in the acidic solution is too low, it is favorable for the recovery of the alcohol with high purity to first subject the solution to flash distillation thereby to obtain a concentrated solution which is suited to precision distillation. After distillation an aqueous solution containing an inorganic salt remains at the bottom of the distillation tower, but there is no problem in treating and disposing of this solution by usual operations.

In the case of recovering a fluorinated alcohol which has a boiling point close to that of water and hence is not easy to separate from water, the alcohol recovered by the neutralization and precision distillation process may contain some moisture. In such a case it is possible to enhance the purity of the recovered alcohol by performing the precision distillation of the acidic solution such that the content of water in the obtained alcohol is not more than about 5%, and preferably not more than $10^3$ ppm, and then reducing the water content to $10^2$ ppm or below by using a suitable desiccant or dehydrating agent such as, for example, anhydrous calcium chloride or molecular sieves.

The following examples relate to the recovery of a fluoroalkyl alcohol.

EXAMPLE 5

The absorption operation of Example 1 was continued until 400 g of HFIP was absorbed into 1 kg of 10 wt % aqueous solution of NaOH. Then 260 g of 35% hydrochloric acid was added to the alkali solution thereby to adjust pH of the solution to 5. The resultant acidic solution was subjected to precision distillation. As the result 372 g of HFIP was recovered. The recovery was 93% on the basis of the quantity of HFIP in the treated solution. In the recovered HFIP the content of moisture was 120 ppm.

EXAMPLE 6

Air containing HFIP was washed with 850 g of 20 wt % aqueous solution of NaOH by the same method as in Example 1 until 660 g of HFIP was absorbed into the solution. Then 440 g of 35% hydrochloric acid was added to the alkali solution thereby to adjust pH of the solution to 5. The acidified solution was subjected to precision distillation. As the result, 620 g of HFIP containing 80 ppm of moisture was recovered. The recovery was 94% on the basis of the quantity of HFIP absorbed in the alkali solution.

EXAMPLE 7

The absorption operation of Example 4 was continued until 100 g of trifluoroethanol was absorbed into 420 g of 10 wt % aqueous solution of NaOH. Then 110 g of 35% hydrochloric acid was added to the alkali solution thereby to adjust pH of the solution to 5, and the acidified solution was subjected to flash distillation to obtain 98 g of crude trifluoroethanol. By precision distillation of the crude alcohol 90 g of trifluoroethanol was recovered. The recovery was 90% on the basis of the quantity of trifluoroethanol in the alkali solution. The recovered trifluoroethanol contained 5200 ppm of water, but the content of water could be reduced to 150 ppm by a dehydrating treatment with 10 g of molecular sieves.

EXAMPLE 8

The absorption operation in Example 7 was modified by using 20 wt % aqueous solution of NaOH in place of the 10 wt % solution. In this case 100 g of trifluoroethanol was absorbed into 210 g of the alkali solution. Then 110 g of 35% hydrochloric acid was added to the alkali solution thereby to adjust pH of the solution to 5, and the acidified solution was subjected to precision distillation. As the result 92 g of trifluoroethanol was recovered. The recovery was 92% on the basis of the quantity of the alcohol in the alkali solution. The recovered trifluoroethanol contained 7000 ppm of water, but the water content could be reduced to 200 ppm by a dehydrating treatment with 10 g of molecular sieves.

What is claimed is:

1. A method for removing a fluoroalkyl alcohol from a waste gas, wherein said fluoroalkyl alcohol is selected from the group consisting of trifluoroethanol, pentafluoropropanol and hexafluoroisopropanol, the method comprising the step of bringing the waste gas into contact with an aqueous basic solution having a concentration in the range from 10 to 30% by weight of a base selected from the group consisting of alkali metal hydroxides, alkali metal carbonates, alkaline earth metal hydroxides and alkaline earth metal carbonates, thereby to absorb the fluoroalkyl alcohol into said solution and consequently obtain an aqueous basic solution containing an alkoxide of the fluoroalkyl alcohol.

2. A method according to claim 1, wherein the waste gas is brought into said aqueous basic solution at room temperature.

3. A method according to claim 1, wherein the waste gas is brought into contact with said aqueous basic solution in a tower packed with means for dispersing fluids by flowing the waste gas through the tower upward and flowing the aqueous basic solution through the tower downward.

4. A method for removing a fluoroalkyl alcohol from a waste gas and recovering the fluoroalkyl alcohol, wherein said fluoroalkyl alcohol is selected from the group consisting of trifluoroethanol, pentafluoropropanol and hexafluoroisopropanol, the method comprising the steps of:

(a) bringing the waste gas into contact with an aqueous basic solution having a concentration in the range from 10 to 30% by weight of a base selected from the group consisting of alkali metal hydroxides, alkali metal carbonates, alkaline earth metal hydroxides and alkaline earth metal carbonates, thereby to absorb the fluoroalkyl alcohol into said solution and consequently obtain an aqueous basic solution containing an alkoxide of the fluoroalkyl alcohol;

(b) adding an acid to the aqueous basic solution obtained at step (a) until the basic solution turns into an acidic solution with a pH value smaller than 5, thereby to turn said alkoxide into said fluoroalkyl alcohol; and (c) subjecting said acidic solution obtained in step b) to distillation, thereby to recover said fluoroalkyl alcohol.

5. A method according to claim 4, wherein at step (a) the waste gas is brought into said aqueous basic solution at room temperature.

6. A method according to claim 4, wherein at step (a) the waste gas is brought into contact with said aqueous solution in a tower packed with means for dispersing fluids by flowing the waste gas through the tower upward and flowing the aqueous solution through the tower downward.

7. A method according to claim 4, wherein said acid is an inorganic acid.

8. A method according to claim 7, wherein said inorganic acid is selected from the group consisting of hydrochloric acid, sulfuric acid and nitric acid.

9. A method for removing a fluoroalkyl alcohol from a waste gas, wherein said fluoroalkyl alcohol is selected from the group consisting of trifluoroethanol, pentafluoropropanol and hexafluoroisopropanol, the method comprising the step of bringing the waste gas into contact with an aqueous basic solution having a concentration in the range from 10 to 30% by weight of ammonia, thereby to absorb the fluoroalkyl alcohol into said solution and consequently obtain an aqueous basic solution containing an alkoxide of the fluoroalkyl alcohol.

10. A method according to claim 9, wherein the waste gas is brought into said aqueous basic solution at room temperature.

11. A method according to claim 9, wherein the waste gas is brought into contact with said aqueous basic solution in a tower packed with means for dispersing fluids by flowing the waste gas through the tower upward and flowing the aqueous basic solution through the tower downward.

12. A method for removing a fluoroalkyl alcohol from a waste gas and recovering the fluoroalkyl alcohol, wherein said fluoroalkyl alcohol is selected from the group consisting of trifluoroethanol, pentafluoropropanol and hexafluoroisopropanol, the method comprising the steps of:

(a) bringing the waste gas into contact with an aqueous basic solution having a concentration in the range from 10 to 30% by weight of ammonia, thereby to absorb the fluoroalkyl alcohol into said aqueous solution and consequently obtain an aqueous basic solution containing an alkoxide of the perfluoroalkyl alcohol;

(b) adding an acid to the aqueous basic solution obtained at step (a) until the basic solution turns into an acidic solution with a pH value smaller than 5, thereby to turn said alkoxide into said fluoroalkyl alcohol; and (c) subjecting said acidic solution obtained in step b) to distillation, thereby to recover said fluoroalkyl alcohol.

13. A method according to claim 12, wherein at step (a) the waste gas is brought into said aqueous basic solution at room temperature.

14. A method according to claim 12, wherein at step (a) the waste gas is brought into contact with said aqueous basic solution in a tower packed with means for dispersing fluids by flowing the waste gas through the tower upward and flowing the aqueous basic solution through the tower downward.

15. A method according to claim 12, wherein said acid is an inorganic acid.

16. A method according to claim 15, wherein said inorganic acid is selected from the group consisting of hydrochloric acid, sulfuric acid and nitric acid.

* * * * *